United States Patent [19]
Li et al.

[11] Patent Number: 6,004,822
[45] Date of Patent: Dec. 21, 1999

[54] DEVICE AND METHOD FOR MEASURING SOLUBILITY AND FOR PERFORMING TITRATION STUDIES OF SUBMILLILITER QUANTITIES

[75] Inventors: Jianmin Li, Lexington, Mass.; Bradley D. Anderson, Salt Lake City, Utah

[73] Assignee: Alfred LaGreca, Hingham, Mass.

[21] Appl. No.: 09/002,634

[22] Filed: Jan. 5, 1998

Related U.S. Application Data

[60] Provisional application No. 60/042,698, Apr. 4, 1997.

[51] Int. Cl.$^6$ .............................. G01N 1/10; G01N 31/00
[52] U.S. Cl. ........................ 436/177; 436/178; 436/163; 436/164; 422/58; 422/81; 422/99; 422/100; 422/101; 422/103
[58] Field of Search ................................ 422/58, 56, 60, 422/99, 100, 101, 102, 103, 104, 81; 436/177, 174, 178, 163, 164

[56] References Cited

U.S. PATENT DOCUMENTS

| | | | |
|---|---|---|---|
| 2,946,486 | 7/1960 | Gilmont | 222/38 |
| 4,086,062 | 4/1978 | Hach | 422/100 |
| 4,335,638 | 6/1982 | Smolen | 422/81 X |
| 4,743,570 | 5/1988 | Lamont, Jr. | 437/248 |
| 5,045,284 | 9/1991 | Smith et al. | 422/81 |
| 5,156,811 | 10/1992 | White | 422/100 |
| 5,240,680 | 8/1993 | Zuckermann et al. | 422/67 |
| 5,364,595 | 11/1994 | Smith | 422/100 |
| 5,496,523 | 3/1996 | Gazit et al. | 422/100 |
| 5,552,325 | 9/1996 | Nochumson et al. | 436/177 |
| 5,603,900 | 2/1997 | Clark et al. | 422/101 |
| 5,635,358 | 6/1997 | Wilding et al. | 435/7.2 |
| 5,711,917 | 1/1998 | Juranas et al. | 422/99 |
| 5,719,052 | 2/1998 | Ito et al. | 435/287.1 |

*Primary Examiner*—Arlen Soderquist
*Attorney, Agent, or Firm*—Cesari & McKenna, LLP

[57] ABSTRACT

Described is a device and method for facilitating the determination of the solubility and dissolution properties of chemical compounds in various solvents. The device uses submilliliter quantities of a solvent and correspondingly small amounts of the chemical compound. The device enables solubility measurements to be made on small amounts of chemical compounds, and enables multiple sampling for generating dissolution profiles. The device includes a housing having first chamber in fluid communication with a second chamber. A pump is provided to force alternatingly the solvent from one chamber to another. A filter located between, and in fluid communication with, the first and second chambers allows flow of a solution of the solvent and the chemical compound between the chambers, and the filter prevents the passage of undissolved compound. The device may also be used for titration studies of submilliliter quantities of solutions or suspensions.

35 Claims, 6 Drawing Sheets

DEVICE AND METHOD FOR MEASURING SOLUBILITY AND FOR PERFORMING TITRATION STUDIES OF SUBMILLILITER QUANTITIES

This application claims the benefit of U.S. Provisional Application No. 60/042,698, filed Apr. 4, 1997, and titled "Device and Method for Measuring Solubility and for Performing Titration Studies of Submilliliter Quantities".

BACKGROUND OF THE INVENTION

1. Field of the Invention

This invention relates to a device and method for facilitating measurements of the solubility of organic, inorganic and organic-metallic compounds, and for performing titration studies on small amounts of samples of such compounds, particularly of compounds related to pharmaceutical research and development.

2. Description of the Prior Art

In the field of pharmaceutical research and development, it is almost always necessary to evaluate the general suitability of a newly developed drug candidate prior to launching into full development. Evaluation of the general suitability of such chemical compounds typically includes solubility studies of the compound in various in-vivo compatible or physiologically compatible solvents, as well as other chemical characteristics, such as the determination of the acid dissociation constant ($pK_a$) and solubility profiles at various pH values. Due to the lack of knowledge regarding the fundamental chemical properties of new drug candidates, the cost of purifying or manufacturing such drug candidates is generally extremely high, and therefore the quantities of compound produced in initial research stages are very limited.

The current process for determining the solubility of a given compound in a solvent such as water, for example, is as follows: A 1.5 to 2.0 milliliter (ml) glass vial is selected, into which is placed a known amount of distilled water, typically about 0.5 to 1.0 ml. Then, an amount of the compound is added to the vial, the amount being substantially greater than the amount estimated to be the compound's solubility in water. For example, if it is estimated that a compound's solubility in water is 10 milligrams (mg) per ml, the amount of compound to be added to the vial should be at least 15 to 20 mg. Using substantially more compound than is estimated to be necessary to saturate the solvent insures that when the compound-solvent system has reached equilibrium, there will remain in the vial at least some amount of undissolved compound. Following the introduction of the compound into the vial, the vial is capped and the vial is placed in a rotor/shaker. The temperature is held at a constant temperature, commonly either 25 or 37 degrees Centigrade, and the vial is shaken or rotated for a certain period of time, typically at least 24 hours.

After the certain period of time, the sample is inspected to verify that solid compound remains in the vial. If no solid compound remains, the process must be reinitiated with additional compound and the vial must again be shaken for a certain period of time. Assuming that solid compound remains, the solid compound and solution are separated by either filtration or centrifugation.

Filtration is usually performed by hand using a standard syringe and syringe-adaptable filter. Regarding the filter used, it is generally necessary to predetermine the degree of adsorption of the compound on the filter during filtration. If the compound in question has a density different from the solution, centrifugation may be employed. Preliminary analysis is necessary in order to determine the necessary centrifugal force to ensure complete separation. After separation by either filtration or centrifugation, the concentration of the compound in the solution is determined by a suitable analytical method to arrive at its solubility.

There are numerous drawbacks with current methods (and related devices) for evaluating the solubility of a compound in a particular solvent. The primary drawbacks are threefold. First, the current methods and devices require relatively large quantities of solvent which in turn means that relatively large amounts of compound are necessary. Second, the current methods and devices require a time-consuming and wasteful process of separation of the saturated solution from the undissolved compound. More specifically, if filtration is used, compound adsorption on the separation filter must be considered. If centrifugation is used, centrifugation speed and material densities must be determined, and the possibility that fine particles of solid remain in the supernatent must be considered.

The third and perhaps most significant drawback with the present methods and devices is the repetition of the above-described process. The entire process described above is normally repeated for various periods of time to insure an accurate and complete solubility measurement. For example, FIG. 1 shows a typical solubility curve 101 over a period of time for a typical chemical compound in a solvent such as water. With respect to FIG. 1, it is readily appreciated that to accurately measure the solubility of the chemical compound, it is very important to allow the chemical compound to mix with the solvent for a sufficiently long period of time in order to reach an equilibrium solubility 102. However, because the chemical compound is "new" and many of its chemical properties are unknown, the amount of time necessary to attain such saturation of the solvent is uncertain. Furthermore, as seen in FIG. 2, not all solubility curves 111 simply approach the equilibrium saturation plateau 112. The solubility curve 111 in FIG. 2 has a local maximum (or overshoot) solubility at point 113, however, point 113 is not the equilibrium solubility of the compound in the solvent.

Thus, repetition of the solubility analysis further consumes additional quantities of compound. To further illustrate the relatively large quantities of chemical compound required in the aforesaid normal or standard practice, if five different solvents are intended to be evaluated for their solubility properties with respect to a particular compound, the average solubility of the compound in each solvent is estimated to be 10 mg/ml, and the quantity of solvent to be used is 0.5 ml, at least 35 to 50 mg of the compound will be required. Furthermore, to assure accuracy (see, e.g., FIGS. 1 and 2), the samples should be tested in triplicate, which will consume 105 to 150 mg of compound for a solubility study in only five different solvents. Moreover, if the compound needs a long period of time to reach equilibrium, an additional amount of compound would be required to repeat the testing. As explained above, however, the available quantities of newly developed compounds are very limited. In the preparation of new compounds for pharmaceutical research, it is not uncommon to be limited to 200 mg or less for solubility and characterization studies, which may not even be enough to generate the basic solubility data.

Therefore, it is very important to consume as little compound as possible while repetitively measuring the solubility of the compound in the solvent over different periods of time to insure that the equilibrium saturation point has been reached. It is also important to repetitively measure the solubility of the compound to insure accuracy of the prior measurements. These repetitive measurements, each using relatively large amounts of chemical compound, demonstrate a major shortcoming of the aforementioned current practice of measuring solubility.

In view of cost, availability and accuracy factors, it would be desirable to use small amounts of the subject chemical compound and correspondingly small amounts of solvent for studies involving solubility. It would be desirable to eliminate the separation step before determining the concentration of the compound in the solution. It would also be desirable to generate a solubility curve (again see, e.g., FIGS. 1 or 2) during the solubility study while keeping the necessary amount of compound to a minimum.

Titration, another common analysis performed on solutions of new chemical compounds, is generally performed by adding a given amount of acid or base solution into the solution. After thoroughly mixing the solution and assuming it reaches equilibrium, the pH value of the mixed solution is determined using a pH-electrode. These steps are repeated until the final solution reaches a desired pH. Due to the requirement of thorough mixing, the volume of solution in a titration study is normally in the range of milliliters. It would be desirable to reduce the volume of solution required for a titration study.

Another type of titration study, commonly called "suspension titration", involves evaluating the solubility of solid compounds suspended in a solvent, at various pH values of the solvent. Suspension titration is a combination of the previously described solubility and pH titration procedures. Following the addition of an acid or base titrant to the suspension of a given acidic or basic compound, the pH is monitored until a constant value is obtained (indicating that equilibrium has been established). The concentration of the dissolved solute is then determined as described above. Another aliquot of acid or base is then added and pH is again monitored until a constant value is again attained. Solute concentration is then again determined at this new pH. By repeating this procedure until the desired pH range is fully covered, a pH solubility profile can be derived using the same solid sample of the compound for all points. A typical pH solubility profile is illustrated in FIG. 5.

Devices for performing titration, sampling and solubility measurements on small quantities of materials have been described in the prior art. For example, U.S. Pat. No. 2,946,486 to Gilmont describes an analytical device for titrating functions comprising a micro-buret having capillary tubing at one end and an enlarged chamber at the other end.

U.S. Pat. No. 4,086,062 to Hach shows a liquid dispensing device for chemical titration having a reciprocating plunger for expelling fluid from an attached titrating solution cartridge.

U.S. Pat. No. 4,743,570 to Machler et al. shows a flow-through cuvette having a very small volume for use in high-pressure liquid chromatography.

Further, Smith et al. in U.S. Pat. No. 5,045,284 disclose a flow injection analysis flow cell for titration flow injection analysis.

Upon consideration of the aforementioned disclosures, it will be observed that none of the described inventions and patents, taken either singly or in combination, may be regarded to describe or to suggest the instant invention as claimed.

Accordingly, it is a principal object of the invention to provide a device and a method for facilitating measurements of the solubility of chemical compounds in various solvents, wherein such compound samples are present in small amounts.

It is another object of the invention to provide a device and method for determining various characteristics of solutions, particularly of compounds in solution, and in particular, for example, the pH of solutions wherein such solutions are present in submilliliter amounts.

It is another object of the invention to provide a device and method for determining various characteristics of solutions without an additional or separate procedure for separating the saturated solution from the undissolved chemical compound.

It is yet another object of the invention to provide improved elements and arrangements thereof in an apparatus for the purposes described which is inexpensive, dependable and fully effective in accomplishing its intended purposes.

SUMMARY OF THE INVENTION

The foregoing objects are among those attained by the invention, which provides in one aspect a device for facilitating the determination of the solubility and dissolution properties of chemical compounds in various solvents. The device includes a housing having a first and second chamber in fluid communication with each other, a pump coupled to at least one of the chambers for pumping alternatingly the solvent from one chamber to another, and a filter in fluid communication with and disposed between the chambers for allowing flow of the solution from one chamber to another. The filter prevents undissolved compound from passing from one chamber to another.

In a further aspect of the invention, the chambers include capillary tubes extending towards the filter. The first chamber is adapted to receive the chemical compound. Either of the chambers may be adapted to receive the solvent. Upon activation of the pump, the filter prevents undissolved compound from passing from the first chamber to the second chamber. The second chamber is adapted to allow removal of the solution therein. The solution in the second chamber is free of undissolved chemical compound.

Another aspect of the invention provides a pump with a piston for positively displacing the solution in the chambers. The pump further includes first and second pistons corresponding to the first and second chambers. The device may further include a piston driver for activating the pistons and to control piston activation such that the pistons operate out of phase with each other.

In still further aspects, the filter comprises a layer or multiple layers of analytical filter membrane. The filter preferably has a pore size less than 10 micrometers. Portions of the device, including the housing and the chambers may be disposable.

In another aspect, the device includes a one-way valve and detector in fluid communication with the chambers for performing titration studies. Tubing connects the chambers with the one-way valve and forms a continuous loop through the chambers. A detector is provided to measure a characteristic of the solution flowing in the loop.

Still further aspects of the invention provide methods for operating a device of the type described above in order to analyze the solution.

These and other aspects of the invention are evident in the drawings and in the description that follows.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is primarily directed to devices and to methods for aiding in determining the solubility of small amounts of chemical compounds. Further, the invention is directed to devices and methods for performing titration studies on solutions (or suspensions) of compounds in small amounts.

The device and method of this invention substantially reduces the quantity of compound and solvent necessary to evaluate certain characteristics of the compound. The total working volume of compound and solvent may be in the range of 10 to 400 $\mu$l and is preferably in the range of 20 to 200 $\mu$l. For example, if it is assumed that a 50 $\mu$l volume quantity will be tested using the invention disclosed herein, only 10% of the total amount of compound used in the same type of study under the previously described standard method will be needed. The method and device of this invention not only totally or substantially eliminates the manual separation steps of the traditional method, but also makes possible a continuous or multiple sampling process. Such continuous sampling eliminates the necessity of repeating the testing for compounds that need a long duration of time to reach equilibrium with the solvent. This multiple sampling capability may significantly reduce analysis time because equilibrium will be more quickly determinable. Also, solubility versus pH profiles can be generated from a single sample.

The device described herein for use in determining the solubility of chemical compounds may also be conveniently used for titrating small or submilliliter amounts of solutions of compounds. Such titrations are frequently performed in both pharmaceutical laboratories and in ordinary analytical chemistry laboratories. Furthermore, if the device of the invention is attached, coupled or associated in working relationship with a suitable detector and controller, the device may be operated in an automatic mode for determining both solubility and for performing titrations.

Figure 3:
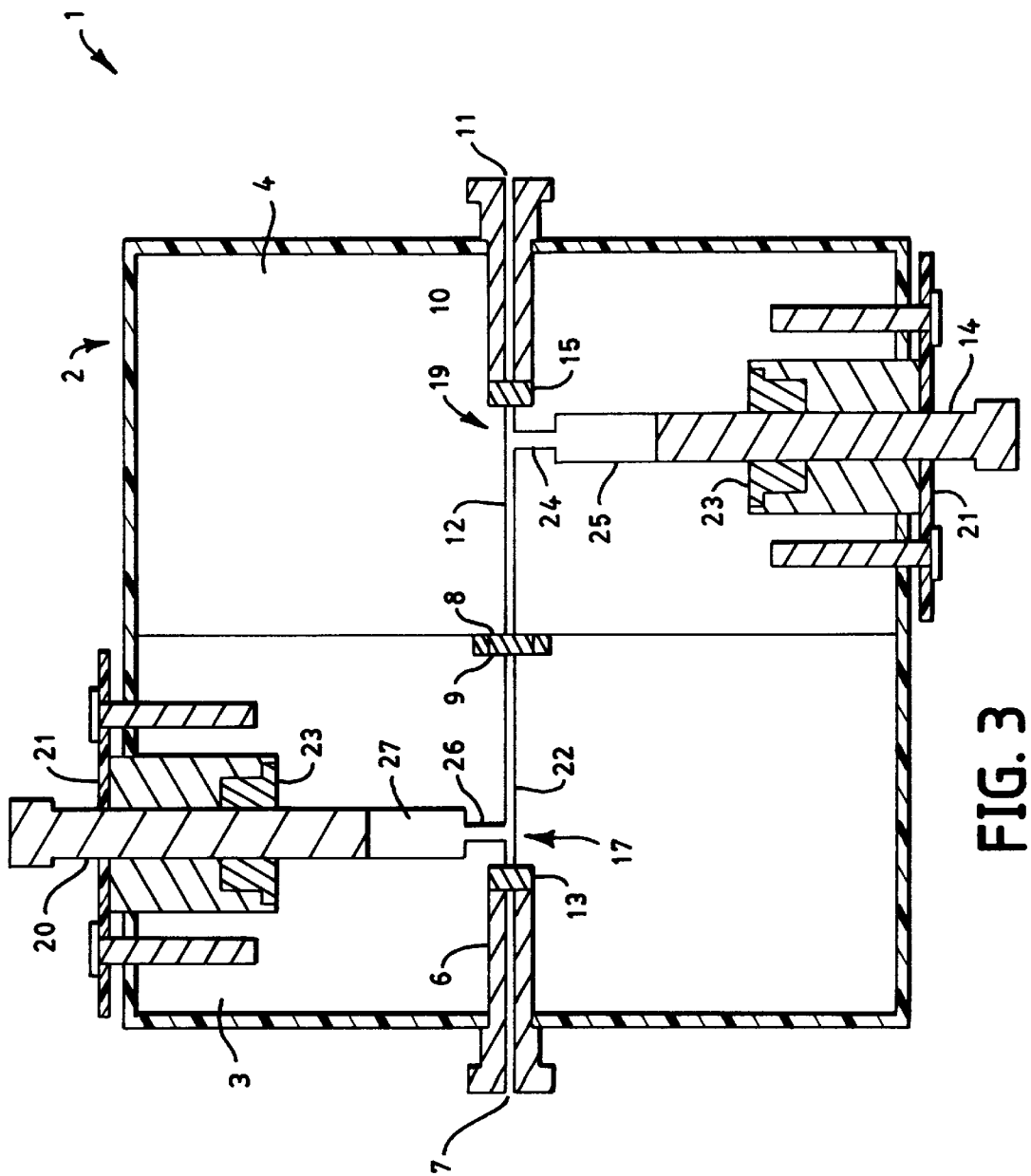
FIG. 3 is a cross-sectional view of a device for determining the solubility of small amounts of chemical compounds in accordance with the present invention.

Thus, more fully described, the invention relates to a device for testing small amounts of compounds and solutions to measure or determine selected physical and chemical characteristics. To this end, shown in FIG. 3 is a device 1 including a housing 2 comprised of two major halves or components, 3 and 4, each half having side walls and an end wall. The two major components identified as 3 and 4 may be substantially identical or very similar. The two halves, when fitted together, form a small three-dimensional x, y and z. The halves 3 and 4 may be secured together by any conventional fastening means. The material used to form the walls and sides of the device may be a synthetic polymer material such as polymethyl methacrylate polymer. However, other suitable solid polymer compositions or materials may be used. It is convenient to make the walls of the device out of transparent materials to enable inspection of internal components.

The housing 2 is fitted with two openings allowing for the positioning of caps 6 and 10 which enable the introduction of solvents and chemical compounds. The caps 6, 10 may be threadably engaged with the housing or affixed to the housing in some other suitable manner. The caps 6, 10 may include channels 7, 11 to facilitate introduction of the solvent and compound. Septa 13, 15 provide a seal between the caps and the housing 2. Each septum 13, 15 may be of a conventional material such as rubber to allow a syringe to pierce the septum and remove solution from the interior of the housing 2. Either or both septa 13, 15 may also be used to introduce a micro-pH electrode to determine the pH value of the solution during testing.

The housing 2 includes two chambers 17, 19 in which the solvent and/or the compound is received. The chambers include capillary tubes 22, 12 that extend from the caps 6, 10, respectively. The chambers also include cylinders 25, 27 each adapted to receive a piston. The capillary tubes 12 and 22 are attached to short tubes or arms 24 and 26 at angles thereto adapted to connect to piston cylinders 25 and 27. The distal ends of capillary tubes 12 and 22 may abut the septa 15 and 13. The opposite ends thereof connect through a filter cavity 8.

The filter cavity 8 is adapted to receive a filter 9. A suitable filter 9 may be a laboratory analytical filter such as that used in the field of high-pressure liquid chromatography. This type of filter is generally made of materials such as nylon, Teflon, stainless steel, a cellulose derivative, or polycarbonate, and the filter preferably has a pore size of about 0.1 to 10micrometers ($\mu$m). The filter 9 may be any arrangement found in the filter art including multiple membrane layers. The filter is sealed between the two halves 3, 4 of the housing 2 at cavity 8, and the filter 9 may include a seal around its perimeter (not shown) to prevent leaking from the housing.

A pump is coupled to the housing and includes two pistons 14, 20. The pistons 14, 20 engage the cylinders 25, 27 and are mounted to the housing 2 in a typical fashion with a bracket 21 that includes a seal 23. The pistons and the cylinders may have any suitable geometry. The pistons 14, 20 are preferably actuated out of phase. Thus, when piston 14 is on a downstroke thereby positively displacing liquid out of cylinder 25, piston 20 is on an upstroke thereby drawing fluid into cylinder 27. Repetitively actuating the pistons in such an out of phase manner forces solution back and forth from one chamber 17 to the other chamber 19, through the capillary tubes 12, 22 and through the filter 9. This tends to stir and mix the undissolved compound with the solution.

Furthermore, back and forth movement of the solution through the filter tends to dislodge and unclog solid particles of chemical compound from the filter. In addition to the pistons, the filter also serves to stir and mix the solvent or solution with the undissolved compound.

The pistons 14, 20 are actuated by a piston driver (not shown). The piston driver controls and coordinates actuation of the pistons. The piston driver may be programmable, with multiple or variable actuation speeds and forces. Also, more than one piston driver may be employed to actuate the pistons 14, 20.

It will be recognized by those skilled in the art that numerous pumping mechanisms may be employed to move the solution from one chamber to another. For instance, a conventional diaphragm pump (not shown) with a diaphragm located in the cylinder and a piston could be used to pump the solution. The pump may employ a pressurized fluid or an hydraulic fluid to pump the fluid from one chamber to the other.

Portions of the device 1 may be designed for disposability. Such a design may include a removable cartridge within the housing that contains the chambers 17, 19 and/or the cylinders 27, 25. After the cartridge is used with a compound and a solvent, the cartridge may be discarded. This will reduce contamination risks and cleaning costs of the device.

In a method of using the device for performing solubility studies, the following procedure may be used:

A filter 9 having a suitable pore size is selected. It is preferable to select a filter 9 that is commonly used in pharmaceutical laboratories for doing high pressure liquid chromatography studies, having a pore size such as 0.5 $\mu$m. The filter is sealed between two halves of the device at cavity 8. At this time, the device should be inspected for leakage.

Next, two pistons 20 and 14 having suitable volumes corresponding to cylinders 25 and 27 are selected and positioned. FIG. 3 shows a seal 23 and bracket 21 for securing the pistons to the housing, however, it should be readily appreciated that other means may be used to secure the pistons to the housing 2 of the device. For example, a clamp or tension fastening means may be used.

A working volume defined by the chambers 17, 19 may range from about 10 to about 400 $\mu$l, and more preferably 20 to about 200 $\mu$l. However, other working volumes may be used depending upon the diameter and stroke distance of the pistons selected by the user.

Next, a suitable amount of a compound to be analyzed is placed within the chamber 17. If there is difficulty in loading the compound, it may be helpful to actuate either or both of pistons 20 and 14.

A prospective solvent to be characterized with the compound may be loaded into the same chamber 17 or the other chamber 19. Activating the pistons may make loading of the compound and the solvent easier. The two pistons may also be actuated to repel air bubbles from inside the chambers 17, 19, the capillary tubes 22, 12, the cylinders 25, 27 and the filter cavity 8.

Next, the device is placed on the piston driver (not shown), and a rate for piston activation is selected and set. A suitable activation rate for piston movement is typically from about 0.1 to about 5 strokes per minute, depending upon the physical-chemical properties of the compound studied and the configuration of the system. The piston driver includes conventional control circuitry. The piston driver is programmable to set the piston activation rate and the relative phase of the piston actuation. It is preferable that the piston driver activates the two pistons 14 and 20 substantially out of phase with each other.

Activation of the pistons will mix and dissolve the compound loaded in chamber 17. The dissolved compound and solvent will form a solution of solvent and compound. The pistons will force the solution through the filter 9 into chamber 19 and the filter will prevent undissolved compound from passing from chamber 17 to chamber 19. Thus, undissolved solid compound will be prevented from entering chamber 19 and only a solution will be present in such chamber 19.

Figure 1:
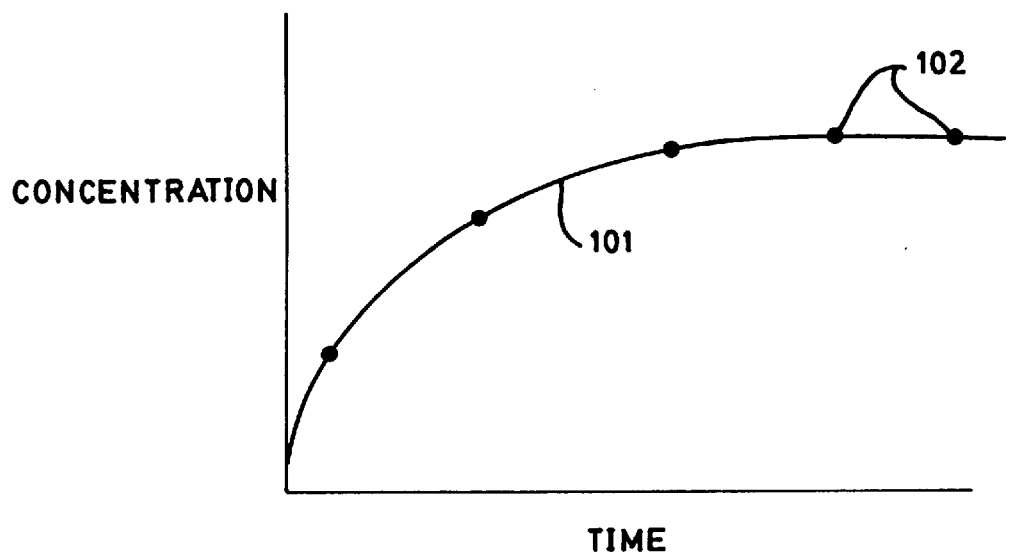
FIG. 1 is a concentration versus time curve for a typical chemical compound in a particular solvent.
Figure 2:
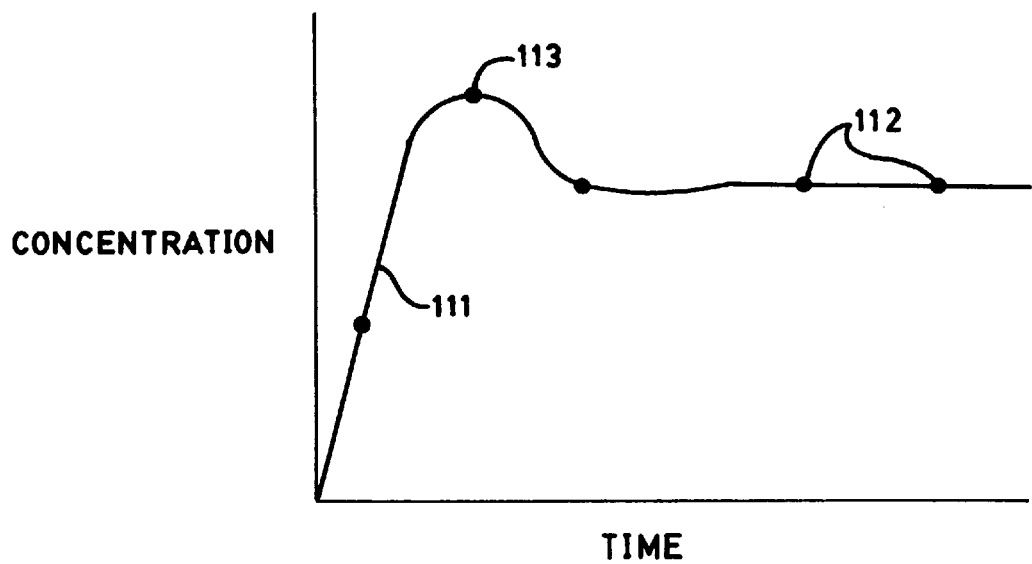
FIG. 2 is another concentration versus time curve for a typical chemical compound in a particular solvent.

Next, after a suitable period of piston cycling, a sample of the saturated solution of compound and solvent is removed from chamber 19, by way of end cap 10 and channel 11 using a micro-syringe. A typical solution sample is about 1 to 20 $\mu$l. The solution in chamber 19 is free of undissolved compound and thus the sample does not require additional separation. The solution withdrawn from chamber 19 may be analyzed by appropriate means to determine its concentration following suitable dilution with known quantities of additional solvent. As explained above with respect to FIGS. 1 and 2, in order to insure that the compound studied has reached equilibrium with the solvent, the steps involving regulated piston movement and sample removal should be repeated.

The device may be used also for micro-titration studies. Such studies are usually required for new compounds having potential drug or medicinal uses, and they are also commonly performed in general chemistry laboratories.

Figure 4:
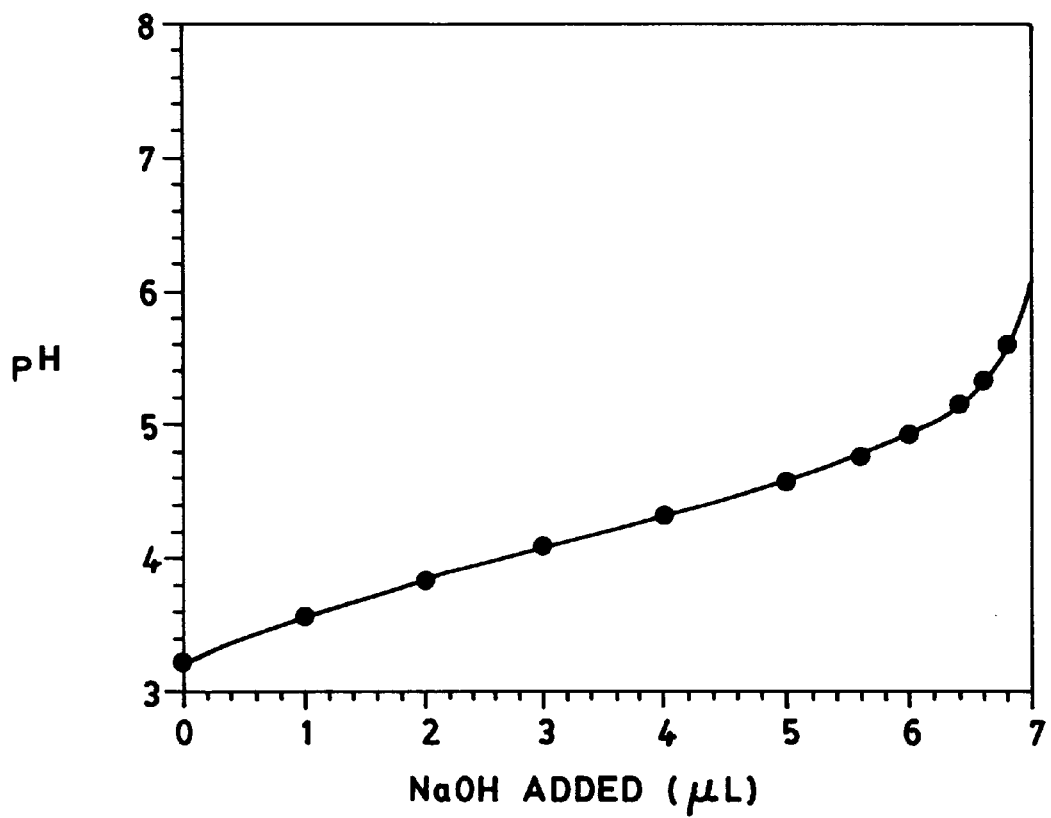
FIG. 4 is a pH versus titrant volume profile for a typical chemical compound.

Referring now to FIG. 4, there is seen a pH-titration profile showing the relationship between solution pH and the amount of acid or base added to the solution. An acid or base is added to the solution by piercing through septum 13 between channel 7 and chamber 22. After adding the acid or base to the solution, thorough mixing is required to ensure equilibrium. The pistons 14 and 20 are moved back and forth to force the solution to flow through filter 9 so that the solution and acid or base are well-mixed. The pH value of the well-mixed solution may then be determined with a pH electrode 27 through end cap 10 in chamber 12.

Figure 5:
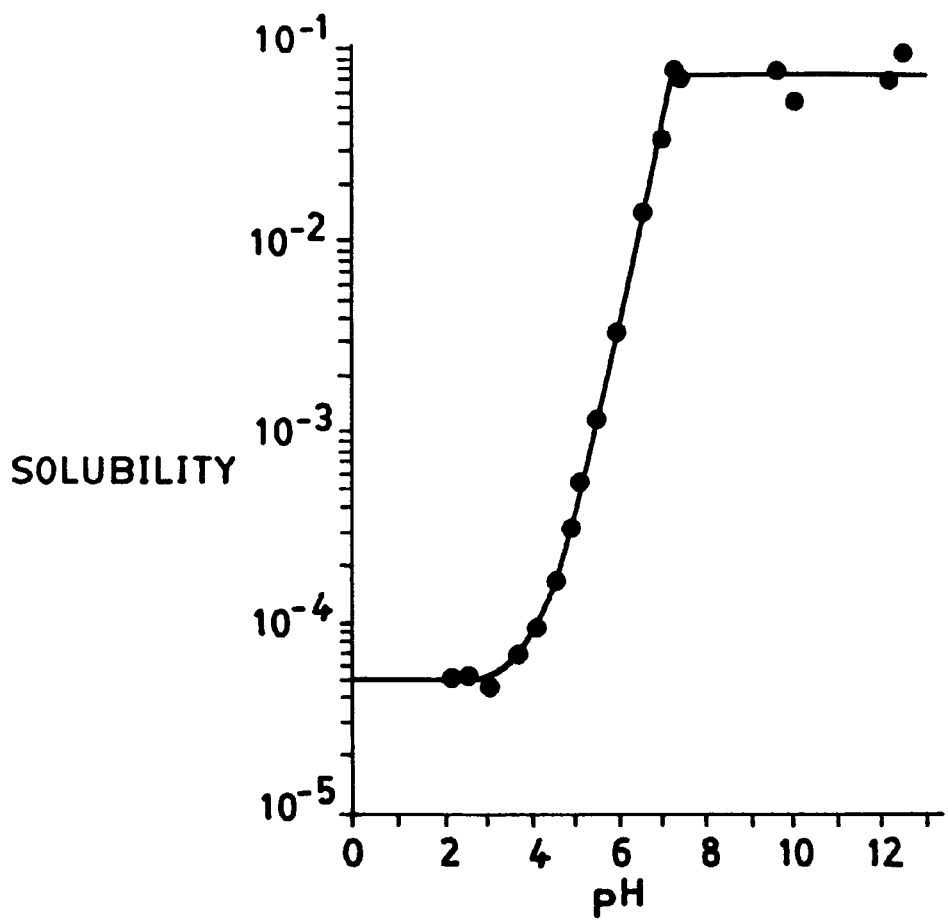
FIG. 5 is a solubility versus pH profile for a typical chemical compound.
Figure 6:
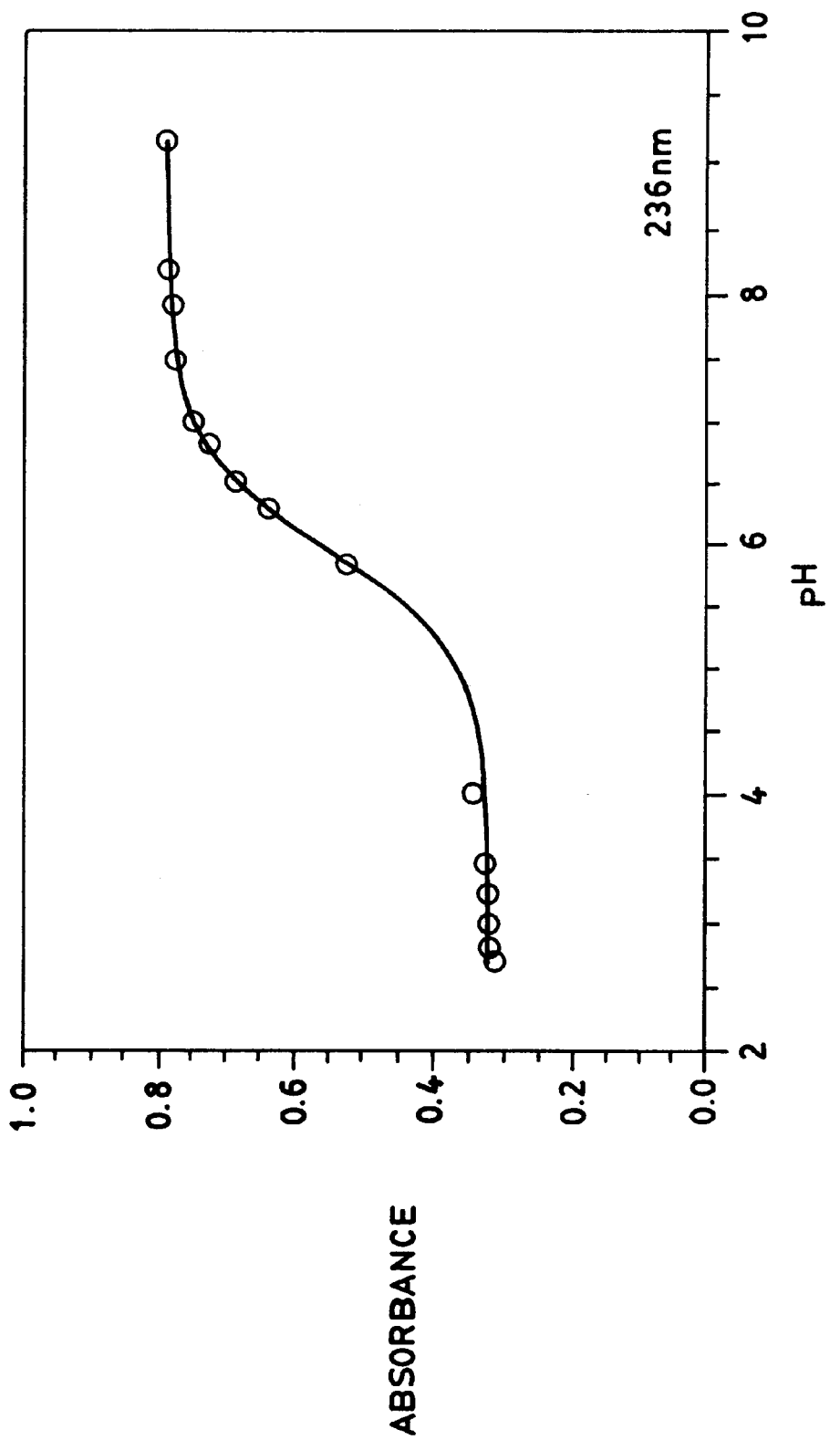
FIG. 6 is an absorbance versus pH profile at a particular wavelength for a typical chemical compound.

Shown in FIG. 5 is a typical curve illustrating the relationship between a solution characteristic, in this case solubility of a chemical compound (on a logarithmic scale), and the solution pH. Similarly, FIG. 6 depicts a typical curve showing another solution characteristic, the relationship absorbance at a given wavelength (236 nm), versus the solution pH. Additional solution characteristics may include NMR chemical shift, optical rotation, conformation and others known in the art. To evaluate a solution characteristic against the pH level of the solution, procedures similar to those described above should be followed. First, the solution should be loaded into one of the two chambers. Next, add a given amount of acid or base in the same fashion as discussed above and mix the solution well. Then remove some of the solution, such as 1 to 20 $\mu$l, through cap 10 and septum 15 with a micro-syringe by coupling the device 1 to additional components. The additional components and a procedure for use therewith are more fully described below.

Figure 7:
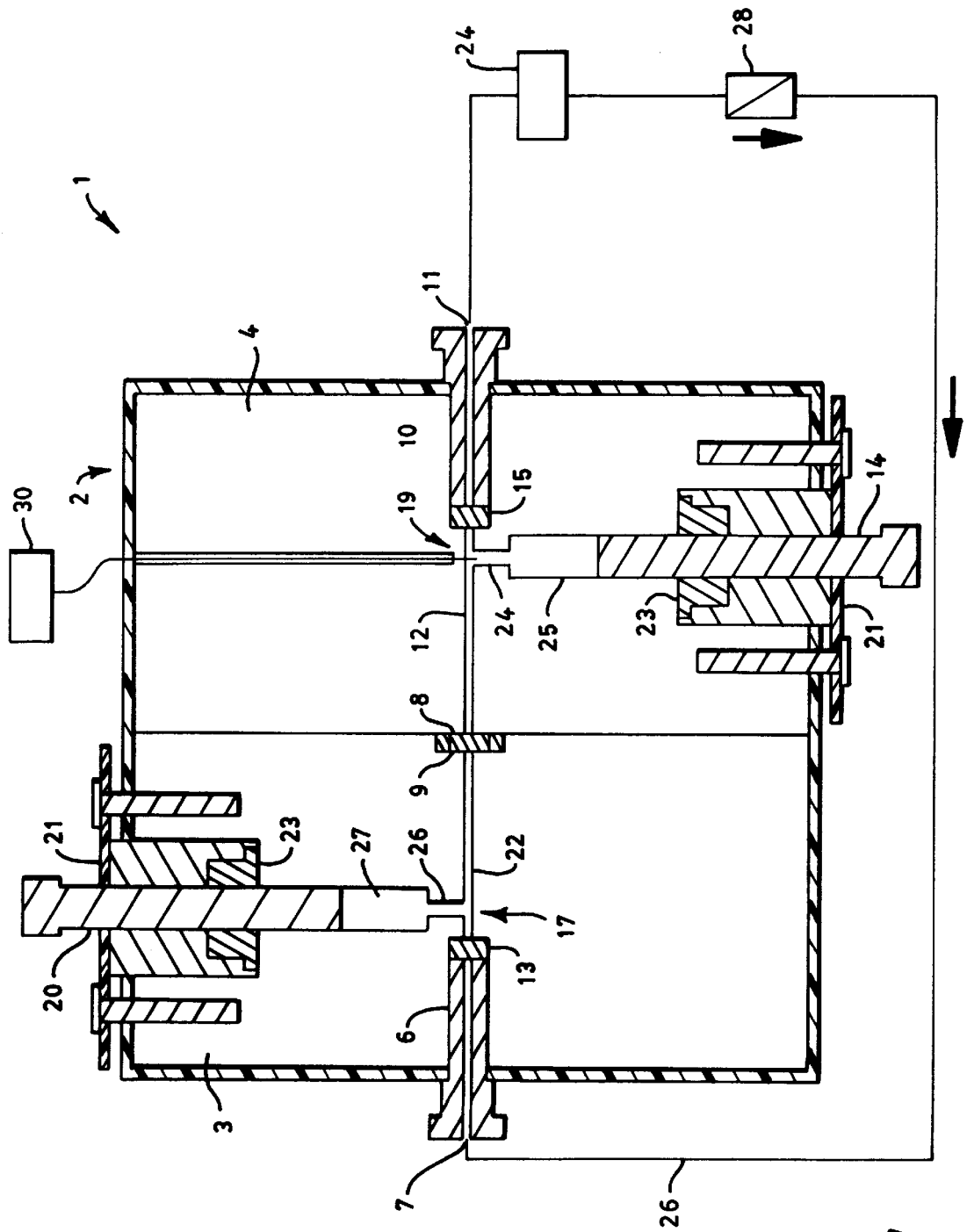
FIG. 7 is a cross-sectional view of a device for performing titration analyses on submilliliter solutions.

Referring now to FIG. 7, suitable tubing 26 is connected to channels 7 and 11 to connect the chambers 17, 19. The tubing 26 allows a continuous closed-circuit flow of solution from the chamber 17, through the filter 9, to the chamber 19, and then back to chamber 17. A one-way valve 28 is located in the tubing line 26. When one-way valve 28 is closed, actuation of the pistons agitates the solution back and forth between the chambers and through the filter. When the one-way valve 28 is open, the solution flows through the continuous loop from the chamber 17, through the filter 9, to the chamber 19, and then back to chamber 17.

The tubing 26 and one-way valve 28 allows the solution to flow to detectors or other measuring devices. Such a detector 24 may be a spectroscopic instrument employing an ultraviolet light source or an automated solubility analysis device. A micro-pH electrode 29 is attached to a suitable pH meter 30. The pH electrode 29 may be introduced through the housing half 4 or through the septum 15 for determining the pH of the solution in the system. It should be recognized by those skilled in the art that the detector 24 and the pH-electrode 29 may be located at a number of different locations in the device to suitably measure the desired characteristic and the pH of the solution.

A compound and solvent (or a solution thereof) is loaded into the system through end cap 6, and the chambers 17 and 19 are filled as a result of inward and outward movement of pistons 14 and 20. A micro-syringe (not shown) attached at end cap 6 is filled with a standard acid or base solution depending upon the intended titration protocol. An acid is loaded in the syringe to be used for pH decreases and a base is used for pH increases.

Then, the two pistons 14, 20 should be moved inwardly and outwardly in sequence until a stable pH value is obtained at the pH meter. At this point the one-way valve 28 is opened and a reading is taken from the detector 24.

Once a stable pH value has been achieved and a reading from the detector 24 is taken, a small volume of standard acid or standard base, such as, for example, 1 to 20 µl, is injected from the micro-syringe. The one-way valve 28 should be closed. Piston movement and acid or base injection is repeated until the desired pH has been achieved. Again, switch the one-way valve to the open position and a reading may be taken at the detector 24. In this manner a curve of a solution characteristic versus solution pH, such as that shown in FIGS. 5 or 6, is produced. It should be recognized that greater solution volumes than those previously described may be required to suitably fill the tubing 26, the check valve 28 and the detector 24 with fluid.

The expression "chemical compound" herein means an organic, inorganic or organic-metallic compound. With respect to a liquid, the expression "small amounts" herein means quantities less than 1 milliliter. With respect to a chemical compound, the expression "small amounts" herein means quantities of chemical compound sufficient to saturate small amounts of solvent.

It should be understood that the preceding is merely a detailed description of certain preferred embodiments. It therefore should be apparent to those skilled in the art that various modifications and equivalents can be made without departing from the spirit or scope of the invention. For example, because the pump serves to move the solution from one side of the filter to the other, many different pumping arrangements may be used including a positive displacement pump, a diaphragm pump, a pump that utilizes a pressurized gas or hydraulic fluid, or multiple pumps and/or pistons and arrangements thereof. Other such modifications and equivalents will be apparent to those skilled in the art.

We claim:

1. A device suitable for facilitating analysis of a solution of small amounts of chemical compound and solvent, said device comprising:
   a housing comprising a first chamber and a second chamber, said first chamber in fluid communication with said second chamber;
   a pump coupled to at least one of said chambers for pumping the solution between said chambers;
   a filter in fluid communication with and disposed between said first and second chambers for filtering solution flowing between said chambers;
   a first cap in fluid communication with said first chamber, said first cap facilitating the introduction of the chemical compound into said housing; and,
   a second cap in fluid communication with said second chamber, said second cap facilitating the introduction of the solvent into said housing.

2. The device in accordance with claim 1, wherein said filter precludes passage of undissolved chemical compound between said chambers.

3. The device in accordance with claim 2, wherein said filter comprises an analytical filter membrane.

4. The device in accordance with claim 3, wherein said analytical filter membrane comprises a pore size of less than 10 micrometers.

5. The device in accordance with claim 2, wherein said filter comprises a plurality of layers of analytical filter membrane.

6. The device in accordance with claim 1, wherein said first chamber comprises a capillary tube extending towards said filter.

7. The device in accordance with claim 6, wherein said second chamber comprises a capillary tube extending towards said filter.

8. The device in accordance with claim 1, wherein said second can comprises means for facilitating the removal of the solution from said second chamber.

9. The device in accordance with claim 8, wherein said second cap further comprises a septum adapted to receive a hypodermic needle.

10. The device in accordance with claim 8, wherein said second cap further comprises a channel adapted to receive a hypodermic needle.

11. The device in accordance with claim 1, wherein said first and second chambers form a working volume of approximately 10 to 400 microliters.

12. The device in accordance with claim 1, wherein said first and second chambers form a working volume of approximately 20 to 200 microliters.

13. The device in accordance with claim 1, wherein said pump comprises a piston for positively displacing the solution.

14. The device in accordance with claim 13, wherein said pump further comprises a diaphragm disposed between said piston and said first chamber.

15. The device in accordance with claim 1, wherein said pump comprises a first piston coupled to said first chamber and a second piston coupled to said second chamber.

16. The device in accordance with claim 15, further comprising a piston driver coupled to said first and second pistons for controlling actuation of said pistons.

17. The device in accordance with claim 16, wherein said piston driver drives said first piston substantially out of phase with said second piston.

18. The device in accordance with claim 1, wherein said pump utilizes a pressurized fluid for displacing the solution between said chambers.

19. The device in accordance with claim 1, wherein said housing further comprises two separate halves secured together with a fastening means, at least one of said halves comprising a cavity to receive said filter.

20. The device in accordance with claim 1, wherein at least a portion of said housing is removable from said device.

21. The device in accordance with claim 20, wherein said removable housing portion comprises said first and said second chambers.

22. The device in accordance with claim 1, further comprising a one-way valve in fluid communication with said first and second chambers.

23. The device in accordance with claim 22, further comprising a first tubing section attached between said first chamber and said one-way valve and a second tubing section attached between said second chamber and said one-way valve to provide a continuous fluid path through said chambers.

24. The device in accordance with claim 23, further comprising a detector in fluid communication with said second chamber for measuring a characteristic of the solution flowing through said continuous fluid path.

25. The device in accordance with claim 23, further comprising a pH meter in fluid communication with said second chamber for measuring pH of the solution flowing through said continuous fluid path.

26. A device for facilitating analysis of small amounts of a solution that includes a chemical compound, said device comprising:
   a housing comprising a first chamber and a second chamber;
   pumping means coupled to at least one said chamber for alternatingly pumping the solution from one said chamber to the other said chamber;
   filtering means disposed between said chambers for preventing passage of undissolved chemical compound from one said chamber to the other said chamber;
   a one-way valve in fluid communication with said first and second chambers; and, tubing attached between said first and second chambers so as to provide a continuous fluid path through said first chamber, said one-way valve, said second chamber, and said filtering means.

27. A method for analysis of a solution of a chemical compound and a solvent, said method comprising the steps of:
   providing a housing having a first chamber in fluid communication with a second chamber;
   inserting the chemical compound into said housing by means of a first cap in fluid communication with said first chamber;
   inserting the solvent into at least one of said chambers;
   alternatingly pumping the solution from one said chamber to the other said chamber for a predetermined period of time;
   retaining undissolved chemical compound within said first chamber by means of a filter disposed between and in fluid communication with said first and second chambers; and
   sampling at least a portion of the solution in said second chamber.

28. The method according to claim 27, wherein said step of sampling at least a portion of the solution in said second chamber comprises the steps of:
   removing at least a portion of the solution from said housing by means of a second cap in fluid communication with said second chamber; and
   testing a property of said removed solution.

29. The method according to claim 28, wherein the property tested is solubility of the chemical compound.

30. The method according to claim 28, wherein the property tested is concentration of the chemical compound in the solution.

31. The method according to claim 28, wherein the property tested is pH of the solution.

32. The method according to claim 28, wherein the property tested is dissolution rate of the chemical compound in the solvent.

33. The method according to claim 28, wherein the property tested is pH of the solution for the purpose of determining $pK_a$ values of the chemical compound.

34. The method according to claim 28, wherein the property tested is absorbance of the solution at a given wavelength.

35. The method according to claim 27, wherein said step of sampling at least a portion of the solution in said second chamber is performed at least twice.

* * * * *